United States Patent [19]
Cote et al.

[11] Patent Number: 4,727,021
[45] Date of Patent: Feb. 23, 1988

[54] HUMAN MONOCLONAL ANTIBODIES TO CYTOKERATIN

[75] Inventors: Richard J. Cote; Timothy M. Thomson; Alan N. Houghton, all of New York, N.Y.; Herbert F. Oettgen, New Canaan, Conn.; Lloyd J. Old, New York, N.Y.

[73] Assignee: Sloan-Kettering Institute for Cancer Research, New York, N.Y.

[21] Appl. No.: 616,271

[22] Filed: Jun. 1, 1984

[51] Int. Cl.[4] ............... G01N 53/00; G01N 33/53; C12N 5/00; A61K 39/00
[52] U.S. Cl. ........................ 435/7; 435/948; 435/172.2; 435/240.27; 530/387; 436/548; 935/99; 935/110
[58] Field of Search .............. 435/7, 240, 948, 172.2, 435/810; 436/548; 260/112 R; 530/387; 935/99, 110

[56] References Cited

PUBLICATIONS

Cote et al., Proc. Natl. Acad. Sci. USA, vol. 80, pp. 2026–2030, Apr. 1983
Houghton et al., J. Exp. Med., vol. 158, pp. 53–65, Jul. 1983.
Moll et al., Cell, vol. 31, pp. 11–24, Nov. 1982.
Lane, J. Cell Biol, 92: 665–673 (1982).
Lane et al., Cold Spring Harbor Symp. Quant. Biol., 46: 387–402 (1981).

*Primary Examiner*—Esther M. Kepplinger
*Assistant Examiner*—Shawn P. Foley
*Attorney, Agent, or Firm*—John P. White

[57] ABSTRACT

Human monoclonal antibodies (HmAbs) capable of reacting with cytokeratin are disclosed. It has been found that HmAbs De8, M54, M307, Hull, C29, Hu22 and Pa24 may be used to detect these cytoskeletal proteins in various cells. By means of these HmAbs the embryological origin of cells may be determined. This information may be used to determine the possible tissue source of metastasized tumors and greatly affects the management of these cancers.

5 Claims, No Drawings

HUMAN MONOCLONAL ANTIBODIES TO CYTOKERATIN

This present invention was wholly or partially made with funds provided by the Department of Human Health and Services. Accordingly, the United States Government has certain rights in this invention.

This invention concerns monoclonal antibodies to intermediate filaments and their use in diagnosis of metathesized tumors.

BACKGROUND

Intermediate filaments (IF) are a class of proteins which are part of a large family of cytoskeletal proteins. Within the class there exist five components which differ according to the embryological origin of the cell in which they are found. Vimentin are found in cells of mesodermal or neuroectodermal origin, cytokeratins are found in cells of epithelial origin, desmin are found in smooth and striated muscle cells, glial fibrillary acidis protein (GFAP) are found in cells of glial origin and neurofliments are found in neuroectodermal cells, nerve cells and neurons. (Kurki and Virtanan, J. Imm. Methods 67:209–223 (1984); Moll, R., et al. Cell. 31:11–24 (1982); Lazarides, et al. Ann. Rev. Biochem. 51:219–250 (1982); Osborn, M., Cell. 31:303–306 (1982)). Other intermediate filaments have been described but they tend to be either congeners or conjugates of the above five main groups. Means have been sought for rapid and simple identification and measurement of IF in tissue specimen. It is of importance in research on the fundamental biochemistry of cells to be able to observe IF in various kinds of cells. Moreover, in the case of cancerous tissues, especially tumors, it is important to known the embryological origin of the cells in the tumor in order to make a better diagnosis and treatment of the tumor. Metastatic deposit of cells can be of several possible sources—breast, lymph node or brain for example—which may be distinguished by embryological origin and hence kind of IF. By measuring IF in an excised tissue specimen, the source of the tumor may be identified. Treatment may be designed accordingly.

Monoclonal antibodies are highly specific, sensitive reagents for identifying proteins. Knowledge about the surface antigenic structure of several types of human cancers has advanced rapidly with mouse monoclonal antibodies as serological probes, and application of these reagents to cancer diagnosis and therapy is underway. Production of human monoclonal antibodies, however, has proved more difficult to achieve. Despite much effort by many laboratories around the world, there are relatively few reports of success in the literature.

Human monoclonal antibodies which recognize cell surface and intracellular antigens derived from lymphocytes of patients with malignant myeloma have been reported (Houghton, et al, J. Exp. Med. July, 1983). Human monoclonal antibodies recognizing other cellular antigens have been made from lymphocytes of normal individuals or individuals having renal cancer, lung cancer, breast cancer or lymphoproliferative disease. (Cote, et al. Pro. Nat'l. Acad. Sci. April, 1983). Other human monoclonal antibodies capable of detecting intracellular components such as IF have been sought.

SUMMARY

Human monoclonal antibodies (HmAbs) capable of reacting with intermediate filaments (IF) are the subject of the present invention. These HmAbs are produced by hyridoma cell lines prepared by fusing lymphocytes from tumor-bearing individuals with human or mouse immortal cell lines. Novel HmAbs produced are Hull, Hu22, and Pa24. It has also been found that HmAbs De8, M54 and M307, reported previously (Houghton, et al. Supra, Cote et al., Supra) are capable of reacting with IF in certain kinds of cells.

IF in human cells may be detected by contacting the cells with HmAb which is capable of reacting with IF therein and observing the reaction between the cells and the HmAb. Thus HmAb M307 detects vimentin in cells of mesenchymal or neuroectodermal origin, HmAbs Hull, Hu22, Pa24 and M54 detect a cytokeratin component of molecular weight about 42 to 50 kilodaltons in cells of epithelial origin, and HmAb De8 detects vimentin, cytokeratin, GFAP neurofilaments, desmin and an IF-like protein having molecular weight about 66 kilodaltons in a wide variety of cell types.

The kind of IF in a cell is determined by embryological origin of the cell. As a result, the HmAbs of the present invention are useful in determining the embryological origin of cells. If, for example, HmAb 307 reacts with IF in a cell, that cell will be of mesenchymal or neuroectodermal origin, since these are the cells which contain vimentin, the IF with which HmAb 307 reacts.

The assay of the present invention comprises contacting a tissue containing human cells with the antibody recognizing intermediate filaments, and observing the antigenic reaction between the monoclonal antibody and the IF. In a preferred embodiment of the present invention the tissue to be assayed is first excised and is then either freshly or after being frozen or embedded in paraffin by methods well-known in the art contacted with said monoclonal antibodies. In this embodiment said antibodies may be tagged with colored groups or color forming substances such as enzymes, preferably peroxidase and its substrates, with fluorescent substances or with radioactive elements by which the location of the antibodies may be traced. Serological assay of excised tissue is also an embodiment of the present invention. Thus passive hemagglutination, antibody inhibition assay, or glycolipid-mediated immune adherence assay may be used. Likewise anti-mouse immunoglobulin assay and Protein A assays may be employed.

Information as to type of tissue is especially useful in the diagnosis of cancer where there is a metasthesized tumor. Tissue may be excised from the tumor and contacted with a HmAb which detects an IF of known embryological origin. Tissues may be typed by embryological origin and the presence of a particular IF will indicate the type present in the excised specimen. This information will greatly affect management of the cancer patient and determine choice of treatment.

DESCRIPTION

The preparation of HmAbs used in the method of the present invention has been reported by the inventors and others (Houghton, et al. J. Exp. Med. (1983)). This publication is hereby incorporated by reference.

Abbreviations: LICR-2, LICR-LON-HMy2; Ig, immunoglobulin; PHA, phytohemagglutinin; FCS, fetal calf serum; PA, protein A; IA, immune adherence; anti-Ig, rabbit antihuman Ig; EBV, Epstein-Barr virus; PBS, phosphate buffered saline; HmAb(s), human monoclonal antibody(ies); IF, intermediate filament; GFAP, glial fibrillary acidic protein.

The following description is intended to illustrate this invention without limiting same in any manner especially with respect to substantially functional equivalents of cell lines described and claimed herein.

Availability of Hybridoma Cell Lines

The cell lines disclosed in the present invention are deposited at the American Type Culture Collection, Bethesda, Maryland and bear the following deposit numbers:

| Sloan-Kettering # | ATCC # |
|---|---|
| C29 | HB8578 |
| Hu11 | HB8566 |
| Hu22 | HB8567 |
| De 8 | HB8239 |
| M307 | HB8235 |
| M54 | HB8234 |

Deposit is for the purpose of enabling disclosure only and is not intended to limit the concept of the present invention to the particular materials deposited.

Cell Lines. The ARH-77 derived LICR-2 human lymphoblastoid line was kindly provided by Drs. M. O'Hare, P. Edwards and A. M. Neville, the London Branch of the Ludwig Institute for Cancer Research. The mouse myeloma line, NS-1, was obtained in 1979 from Dr. U. Hammerling, Sloan-Kettering Institute for Cancer Research. This cell ine is also on deposit at the ATCC (deposit number: TI8-18) Characteristics of these cell lines are:

| CELL LINE | HEAVY CHAIN | LIGHT CHAIN | DOUBLING TIME | KARYOTYPE |
|---|---|---|---|---|
| LICR-2 | $\gamma$ | $\kappa$ | 24 hr | human |
| NS-1 | — | $\kappa$ | 24 hr | mouse |

The cells were cultured in RPMI 1640 supplemented with 7.5% fetal calf serum, 1% nonessential amino acids (GIBCO, Grand Island, NY), 100 U/ml penicillin, 100 g/ml streptomycin and 20 g/ml 8-azaguanine. No growth occurred in medium containing $4 \times 10^{-7}$ M aminopterin.

Source of Lymphocytes. Sterile specimens were obtained from the Pathology Department of Memorial Hospital through the Tumor Procurement Service. Lymphocytes were derived from (a) regional lymph nodes (patients with breast cancer, colon cancer, lung cancer, melanoma, and renal cancer); (b) peripheral blood (six patients with renal cancer and three normal individuals); (c) spleen (four patients with lymphoproliferative disease and one patient with renal cancer); and (d) tumor specimens (four lung cancers, four breast cancers and one malignant plural effusion from breast cancer).

Preparation of Lymphocytes. Tumor, lymph nodes and spleen were freed of surrounding normal tissue under sterile conditions, and the specimens were minced and passed through 500 Mm cell sieves. The resultant suspension was pelleted, resuspended in RPMI 1640, layered on Ficoll-Hypaque (Pharmacia, Piscataway, NJ), and centrifuged at 400 g for 20 min. The interface cell population was washed and used as a source of lymphocytes for fusion. Peripheral blood lymphocytes were similarly separated on Ficoll-Hypaque gradients. Lymphocytes ($1-2 \times 10^6$ cells/ml) were incubated in RPMI 1640 medium with 7.5% FCS at 37° C. for 24-48 hrs prior to fusion.

Cell Fusion. Lymphocytes and the myeloma/lymphoblastoid cells were combined at a 1:1 or 2:1 ratio and washed three times in RPMI 1640. After the Final Wash, the supernatant was decanted and 0.2 ml 42% (w/v) polyethylene glycol (m.w. 4000) [in phosphate-buffered saline (PBS) containing 15% (v/v) DMSO] was added slowly to the cell pellet with gentle mixing for 3 min at 37° C. Ten ml RPMI 1640, 15% FCS, penicillin/streptomycin, nonessential amino acids, $2 \times 10^{-5}$ M 2-mercaptoethanol $1 \times 10^{-4}$ M hypoxanthine and $1.6 \times 10^{-5}$ M thymidine). The cells were incubated overnight at 37° C., pelleted, resuspended in post-fusion medium containing $4 \times 10^{-7}$ M aminopterin and plated in 96 well tissue culture plates (Costar 3596) at a density of $1-2 \times 10^5$ lymphocytes/well on feeder layers of BALB/c or C57BL/6 peritoneal cells ($1 \times 10^5$ cells/well, plated 24-48 hrs previously). The medium was changed once a week, and the cells maintained in the presence of $4 \times 10^{-7}$ M aminopterin for 4-6 weeks.

Fusion Conditions: General Comments. A number of factors in the fusion procedure were analyzed. Because of variability from fusion to fusion, firm conclusions regarding optimal conditions are difficult to reach. However, several factors were found to influence results in a generally consistent fashion. These included: (1) Condition of myeloma/lymphoblastoid lines. The lines were maintained in log phase growth at 85% cell viability; fusions with overgrown cultures resulted in a low frequency of clonal outgrowth. (2) Fusion ratios. Lymphocyte: myeloma/lymphoblastoid cell ratios of 1:1 or 2:1 resulted in 2-8 times greater clonal outgrowth than fusions at 5:1 or 10:1. (3) Time of aminopterin addition. A delay in the addition of aminopterin to the fused cells for 24 hrs resulted in more vigorous growth of clones. (4) Fetal calf serum (FCS). Significant differences in the frequency of clonal outgrowth were found with different lots of FCS. As initially observed by Edwards et al. (Edwards, P.A.W., Smith, C. M., Neville, A. M. & O'Hare, M. J. (1982) Eur. J. Immunol. 12:641-648), some lots of FCS inhibited the growth and clonability of the myeloma/lymphoblastoid cell lines and the growth of Ig-secreting clones derived from fusions. Lots of FCS were therefore prescreened for optimal growth-promoting properties using these cell types. Optimum fusion success rate was obtained with FCS concentrations of about 10% to 15%. (5) Other media supplements. Medium conditioned by several different cell types did not improve the frequency of clonal outgrowth. Supernatant from cultures of peripheral blood mononuclear cells stimulated 4-6 days with PHA and added to the post-fusion medium resulted in a marked reduction in resulting clones.

Results of Fusions with NS-1 and LICR-2. Clones derived from NS-1 generally appeared between 2-4 wks after fusion, while clones derived from LICR-2 and SK0-007 appeared between 4-7 wks after fusion. All but one fusion between human lymphocytes and NS-1 resulted in growth (95%), while 79% of fusions with LICR-2 resulted in growth (Table I). Fusions of LICR-2 with peripheral blood lymphocytes gave the poorest results, with only 60% and 40% of fusions resulting in growth, respectively. For a given number of lymphocytes, fusions with NS-1 resulted in an average of eight times more clones than fusions with LICR-2. There was a statistically significant difference (Student test) in the frequency of outgrowth between clones derived from NS-1 and LICR-2 (p<0005). This relationship was consistent and independent of the source of lymphocytes.

Immunoglobulin Detection and Quantitation. Supernatants were screened for the production of human Ig by an enzyme-linked immunoassay. Falcon 3034 plates were precoated with 10 μl of supernatant from wells containing growing clones and incubated overnight at 4° C. The plates were washed with PBS and 10 μl of alkaline phosphatase conjugated goat antihuman γ, μ or α heavy chain-specific antibody (Sigma Chemical Co., St. Louis, MO) was added to each well (1/100 dilution). For determination of total Ig, the class-specific reagents were combined (final dilution of each reagent 1/100). After a 30 min. incubation at 37° C., the plates were washed, and 10 μl of p-nitrophenyl disodium phosphate (1 mg/ml) in 10% diethanolamine buffer (pH 9.6) was added to each well and incubated for 30 min. at 37° C. Color changes were measured by an Artek Model 210 Reader. The test was specific for each Ig class over a range of 500 ng/ml to 50 g/ml. For detection of intracellular λ or K light chains by indirect immunofluorescence (see below), goat antihuman λ or K light chain antibodies conjugated to FITC (Cappel Laboratories, Cochranville, PA) was used (1/40 dilution).

Serological Assays for Cell Surface and Intracellular Antigens. The protein A (PA), immune adherence (IA) and rabbit antihuman Ig (anti-Ig) red cell rosetting assay and absorption tests for the detection of cell surface antigens have been described previously (Shiku, H., Takahashi, T., Oettgen, H. F. & Old, L. J. (1976) J. Exp. Med. 144:873-881, Pfreundschuh, M. G., Ueda, R., Rauterberg, E. W., Dorken, B. H. & Shiku, H. (1980) J. Immunol. Metho. 37:71-81., Albino, A. P., Lloyd, K. O., Houghton, A. N., Oettgen: H. F. & Old, L. J. (1981) J. Exp. Med. 154:1764-1778. Intracellular antigens were detected by indirect immunofluorescene tests with target cells grown to confluency in Falcon 3034 plates. The plates were washed and the cells fixed with a 1:1 methanol:acetone (v/v) solution for 5 min. at room temperature. 10 μl of the supernatant to be tested was plated into each well and incubated for 1 hour at room temperature. The cells were washed and 10 μl of a goat antihuman Ig conjugated to FITC (DAKO, Copenhagen) was added to each well (1/40 dilution) and incubated for 1 hour at room temperature. After washing, fluorescence was evaluated with a Leitz Dialux 20 fluorescent microscope. The human cell lines used in the serological assays have been described previously (Shiku, H., Takahashi, T., Oettgen, H. F. & Old, L. J. (1976) J. Exp. Med. 144:873-881, Albino, A. P., Lloyd, K. O., Houghton, A. N., Oettgen, H. F. & Old, L. J. (1981) J. Exp. Med. 154:1764-1778, Ueda, R., Ogata, S. I., Morrissey, D. M., Finstad, C. L., Szkudlarek, J., Whitmore, W. F., Jr., Oettgen, H. F., Lloyd, K. O. & Old, L. J. (1981) Proc. Nat'l. Acad. Sci., U.S.A. 78:5122-5126).

Immunoglobulin Secretion: Range and Stability. Wells with growing clones were screened for Ig secretion; 20-80% contained 500 ng Ig/ml supernatant. [The level of λ chain secreted by the LICR-2 line (100 ng/ml) was generally below the sensitivity of our Ig assay. However, the possibility that the production of LICR-2-derived chain may be increased following fusion cannot be excluded. Human and mouse light chains and e heavy chains were not detected in these assays.]

The levels of Ig produced by the clones were similar regardless of the myeloma/lymphoblastoid cell line or the source of lymphocytes. Seventy to 75% of Ig-secreting clones produced between 1-10 μg Ig/ml and 25-30% produced between 11-100 μg/ml. In 80-90% of wells, only one class of Ig could be detected. The relative proportion of clones secreting each of the major Ig classes (IgM, IgG, IgA) was independent of the myeloma/lymphoblastoid fusion partner, but appeared to be influenced by the source of lymphocytes. A difference was found between clones derived from peripheral blood lymphocytes and those derived from axillary lymph nodes of patients with breast cancer. A higher proportion of IgA-secreting clones resulted from fusions with axillary lymph nodes, while the proportion of IgM-secreting clones was generally higher in fusions with peripheral blood lymphocytes.

The stability of Ig secretion by cells derived from fusions with NS-1 and LICR-2 was compared over a 2-3 month period of subculturing, the percentage of cultures continuing to secrete Ig was comparable (62-70%) in the case of the two fusion partners. At four and seven months post-fusion, approximately 50% of cultures from NS-1 and LICR-2 fusions continued to produce Ig. Thirty-two NS-1 and 19 LICR-2-derived cultures secreting Ig at two months were cloned (one cell/well) once or twice and stable Ig-secreting clones could be selected in 70-80% of cases (observation period 5 months).

Specificity of Human Monoclonal Antibodies to IF

Table I gives the specificity for the HmAbs of the present invention along with immunological class and types of cells within which reacting intermediate filaments are found. The IF component with which each HmAb reacts is given at the bottom of the table.

TABLE I

REACTIVITY OF HUMAN MONOCLONAL ANTIBODIES Pa24, Hu11, Hu22, M54, M307 De8 AND C29 ON CULTURED CELLS.

| Immunological Class | Pa24 IgG | Hu11 IgA | Hu22 IgM | M54 IgM | M302 IgM | De8 IgM | C29 IgM |
|---|---|---|---|---|---|---|---|
| Epithelial Cells | + | + | + | + | − | + | + |
| Mesenchymal Cells | − | − | − | − | + | + | − |
| Neuroectodermal Cells | − | − | − | − | + | + | − |
| Hematopoietic Cells | − | − | − | − | + | + | − |

+: positive reactivity by indirect immunoflouresence
−: negative reactivity by indirect immunoflourescence
Pa24, Hu11, Hu22, M54 and C29 react with intermediate filaments of the cytokeratin family.
M307 reacts with the intermediate filament vimentin.
De8 reacts with all classes of intermediate filaments (vimentin, cytokeratins, GFAP, neurofilaments, desmin).

Reactivity with Intermediate Filaments

Cultures from fusions with NS-1 and LICR-2 have been identified that secrete antibody reactive with intermediate filaments. Fusion of peripheral blood lymphocytes from normal individuals as well as from tumor-bearing patients has resulted in cultures reacting with intracellular antigens. Eleven of the cultures have been subcloned two or more times, and have remained stable for antibody production; six clones were derived from fusions with NS-1 and four from LICR-2. Fusion with NS-1 produced HmAbs De8, M54, C29 and M307. Fusions with LICR-2 produced Pa24, Hu11 and Hu22.

Intermediate filaments of cultured human tumor cells were detected by hybrids derived from fusions of human lymphocytes with NS-1 and LICR-2. The lymphocyte source, immunoglobulin class and fusion partner of the HmAbs produced are given in Table II.

The intermediate filament recognized by the HmAbs of the present invention are given in Table III.

Characterization of Clones. Karyotypic analysis of six clones derived from NS-1 fusions with human lymphocytes and secreting human Ig showed both mouse and human chromosomes. The hybrid nature of selected LICR-2 derived clones has been demonstrated by the presence of new species of light and/or heavy chains in the clonal population.

TABLE II

|  | Ig Class | Fusion Partner | Lymphocyte Source |
| --- | --- | --- | --- |
| Pa24 | IgG | LICR-2 | Lymph node, breast cancer |
| Hu11 | IgA | LICR-2 | Lymph node, breast cancer |
| Hu22 | IgM | LICR-2 | Lymph node, breast cancer |
| M54 | IgM | NS-1 | Lymph node melanoma |
| M307 | IgM | NS-7 | Lymph node melanoma |
| De8 | IgM | NS-1 | All Cells with Intermediate filaments |
| C29 | IgM | NS-1 |  |

TABLE III

HUMAN MONOCLONAL ANTIBODIES DIRECTED AGAINST INTERMEDIATE FILAMENTS

| ANTIBODY | Ig CLASS | ANTIGEN DETECTED |
| --- | --- | --- |
| M307 | M | Vimentin |
| M54 | M | Cytokeratin |
| C29 | M | Cytokeratin |
| Hu11 | A | Cytokeratin |
| Hu22 | M | Cytokeratin |
| Pa24 | G | Cytokeratin |
| De8 | M | all classes intermediate filaments |

TABLE IV

HUMAN MONOCLONAL ANTIBODIES REACTIVE WITH INTRACELLULAR ANTIGENS

| CELL LINES | Pa24 |
| --- | --- |
| BREAST CANCER | ●●●●● |
| COLON CANCER | ●●◐○ |
| LUNG CANCER | ●◐●● |
| RENAL CANCER | ●○● |
| BLADDER CANCER | ○○○○○ |
| MELANOMA | ○○○○ |
| ASTROCYTOMA | ○○○ |
| NEUROBLASTOMA |  |
| NORMAL KIDNEY |  |
| FIBROBLASTS |  |

*Each circle represents a different cell line. Results:
● Antigen recognized by this antibody is present.
○ Antigen recognized by this antibody is not detectable
◐ Antigen recognized by this antibody is poorly expressed.
Cell surface antigens assayed by absorption analysis and red cell rossetting technique.
Intracellular components are analyzed by indirect immunofluorescent analysis.

Nine Ig secreting LICR-2-derived clones were examined for intracytoplasmic light chain production by immunofluorescence. Three of nine clones were producing a new light chain in addition to the light chain of the LICR-2; five produced only light chain and one produced only light chain. Analysis by SDS-PAGE has shown and light chains in LICR-2-derived clones.

Phenotyping cells with HmAbs

Cells, excised tissue specimen for example, preferably fresh, frozen or embedded in wax by methods known in the art are contacted with HmAb which is known to react with an IF of given embryological origin. A positive reaction between the antibody and the cell indicates the presence of cells of this tissue type. Table IV gives the reactivity pattern of HmAb Pu24 with various cell lines. From this table, for example, it can be seen that positive reaction of Pa24 with a malignant human cell would indicate the presence of breast, colon, lung, renal, bladder cancer. From this preliminary screening information an appropriate treatment schedule may be prescribed. Other HmAbs to specific IF may likewise be used for screening.

What is claimed:

1. A hybridoma cell line producing a monoclonal antibody which specifically bind to cytokeratin in human cells, said hydridoma selected from the group consisting of C29 (HB8578), Hu11 (HB8566) and Hu22 (HB8567).

2. A human monoclonal antibody produced by a cell lines of claim 1.

3. Method of detecting cytokeratin in human cells comprising contacting said cells with a human monoclonal antibody selected from the group consisting of C29 (HB8578), Hu11 (HB8566) and HU 22 (HB8567) which specifically binds to said cytokeratin and detecting formation of complexes between said monoclonal antibody and said cytokeratin.

4. Method of claim 3 wherein said cells are cultured human cells or an excised tissue specimen from an individual, said tissue specimen being fresh, frozen or embedded in wax.

5. Method of claim 3 wherein said cell is of epitheliel origin.

* * * * *